US007049456B2

(12) United States Patent
Prasad et al.

(10) Patent No.: US 7,049,456 B2
(45) Date of Patent: May 23, 2006

(54) METHOD FOR PREPARING O,O-DIALKYL S-[2-(ALKYLTHIO)ALKYL] PHOSPHORODITHIOATES

(75) Inventors: Vidyanatha A. Prasad, Leawood, KS (US); Robert D. Ingalls, Portage, MI (US); Stephen C. Slahck, Independence, MO (US); Christopher M. Tusa, Raymore, MO (US)

(73) Assignee: Bayer Cropscience LP, Research Triangle Park, NC (US)

( * ) Notice: Subject to any disclaimer, the term of this patent is extended or adjusted under 35 U.S.C. 154(b) by 511 days.

(21) Appl. No.: 10/383,273

(22) Filed: Mar. 7, 2003

(65) Prior Publication Data

US 2004/0176629 A1   Sep. 9, 2004

(51) Int. Cl.
*C07F 9/165*   (2006.01)
(52) U.S. Cl. ........................................................ 558/87
(58) Field of Classification Search ............... None
See application file for complete search history.

(56) References Cited

U.S. PATENT DOCUMENTS

| 2,759,010 | A | 8/1956 | Lorenz et al. | 260/461 |
| 4,283,335 | A | 8/1981 | Minn | 260/326 E |
| 4,283,338 | A | 8/1981 | Minn | 260/326 E |
| 4,416,834 | A | 11/1983 | Feyen et al. | 260/979 |

OTHER PUBLICATIONS

Robert et al., "Reactivity of O,O'-Dialkyldithiophosphoric Acid Towards Different Allylic Compounds," Phosphorus, Sulfur and Silicon and the Related Elements, vol. 97, Iss. 1-4, pp. 83-87 (1994).*
Jaeger et al., "Reactions of a Vesicular Functionalized Surfactant with Alkyl 2-Chloroethyl Sulfides," Langmuir, vol. 16, pp. 9677-9679 (2000).*

* cited by examiner

*Primary Examiner*—Kamal A. Saeed
*Assistant Examiner*—Andrew B. Freistein
(74) *Attorney, Agent, or Firm*—Richard E. L. Henderson

(57) ABSTRACT

The invention relates to a method of preparing O,O-dialkyl S-[2-(alkylthio)alkyl] phosphorodithioates by treating O,O-dialkyl dithiophosphoric acids with a base in the substantial absence of organic solvent to obtain O,O-dialkyl dithiophosphoric acid salts that are in turn treated with thioalcohol derivatives to form the O,O-dialkyl S-[2-(alkylthio)alkyl] phosphorodithioates.

21 Claims, No Drawings

METHOD FOR PREPARING O,O-DIALKYL S-[2-(ALKYLTHIO)ALKYL] PHOSPHORODITHIOATES

BACKGROUND OF THE INVENTION

The invention relates to a method for preparing O,O-dialkyl S-[2-(alkylthio)alkyl] phosphorodithioates. More particularly, the invention relates to a method of preparing O,O-dialkyl S-[2-(alkylthio)alkyl] phosphorodithioates by treating an O,O-dialkyl dithiophosphoric acid with a base in the substantial absence of organic solvent to obtain an O,O-dialkyl dithiophosphoric acid salt that is in turn treated with a thioalcohol derivative to form the O,O-dialkyl S-[2-(alkylthio)alkyl] phosphorodithioate.

O,O-dialkyl S-[2-(alkylthio)alkyl] phosphorodithioates, such as O,O-diethyl S-[2-(ethylthio)ethyl] phosphorodithioate, can be used as pesticides. The compounds are active against insect pests such as aphids, mites, leafhoppers, flea beetles, bean beetles, potato beetles, and thrips.

U.S. Pat. No. 2,759,010 discloses a process for preparing esters of dithiophosphoric acid by reacting O,O-dialkyl dithiophosphoric acids, either as alkali metal salts or in the presence of acid-binding agents, with a compound of the formula $hal(CH_2)_x$-S-$C_yH_{2y+1}$. U.S. Pat. No. 2,759,010 teaches the use of solvents such as benzene, ketone, and alcohols and exemplifies reacting O,O-diethyl dithiophosphoric acid with β-chloroethyl ethyl sulfide in the presence of benzene and pyridine.

U.S. Pat. No. 4,416,834 discloses a process for preparing compounds of the formula

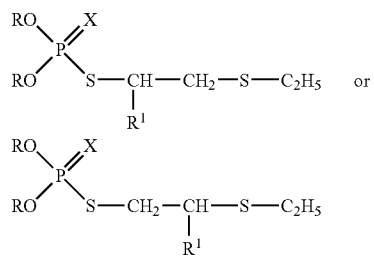

by reacting a dialkyl thiophosphate salt with an ethylmercapto compound. U.S. Pat. No. 4,416,834 teaches that the dialkyl thiophosphate salt is prepared by reacting a dialkyl phosphite with sulfur in the presence of on organic solvent, such as toluene or xylene, followed by treatment with an aqueous base.

U.S. Pat. Nos. 4,283,335 and 4,283,338 teach processes for preparing O,O-dialkyl dithiophosphoric acid esters by reacting an O,O-dialkyl dithiophosphoric acid with an organic chloride that contains at least one acid-replaceable chlorine atom on a carbon atoms attached to oxygen, sulfur, or nitrogen by a single bonds, such as dichloro-p-dioxanes, in the presence of a catalytic amount of zinc chloride, ferrous chloride, or stannous chloride.

Because handling organic solvents may be difficult and/or costly, a need exists for methods of producing O,O-dialkyl S-[2-(alkylthio)alkyl] phosphorodithioates that do not require the use of organic solvents such as toluene or xylene.

Accordingly, it is an object of the present invention to obviate problems of the prior art. The present invention provides a method of producing O,O-dialkyl S-[2(alkylthio) alkyl] phosphorodithioates that does not require the use of organic solvents, such as toluene or xylene, and produces lower levels of by-products, thereby also providing advantageous environmental and economic benefits.

SUMMARY OF THE INVENTION

The invention relates to a method of preparing an O,O-dialkyl S-[2-(alkylthio)alkyl] phosphorodithioate having the formula

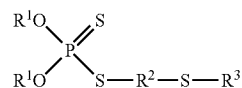

wherein
each $R^1$ is independently $C_1$–$C_4$ alkyl (preferably $CH_3$, $C_2H_5$, n-$C_3H_7$, or i-$C_3H_7$, more preferably $C_2H_5$),
$R^2$ is $C_1$–$C_4$ alkylene (preferably $CH_2$ or $C_2H_4$, more preferably $C_2H_4$), and
$R^3$ is $C_1$–$C_4$ alkyl (preferably $CH_3$ or $C_2H_5$, more preferably $C_2H_5$), comprising (a) treating an O,O-dialkyl dithiophosphoric acid of the formula:

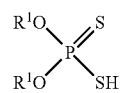

wherein each $R^1$ is independently $C_1$–$C_4$ alkyl, with a base in the substantial absence of organic solvent to obtain an O,O-dialkyl dithiophosphoric acid salt of the formula:

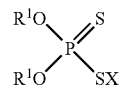

wherein
each $R^1$ is independently $C_1$–$C_4$ alkyl, and
X is a cation (preferably an alkali metal or alkaline earth metal ion, ammonium ion, or a tertiary or quaternary ammonium ion, most preferably $Na^+$, $K^+$, or $NH_4^+$), and (b) reacting the O,O-dialkyl dithiophosphoric acid salt with a thioalcohol derivative having the formula:

wherein
$R^2$ is $C_1$–$C_4$ alkylene,
$R^3$ is $C_1$–$C_4$ alkyl, and
Y is a leaving group (preferably a halogen or a sulfonate, more preferably chlorine).

DETAILED DESCRIPTION OF THE INVENTION

The method of the invention is advantageous in that the treatment of the O,O-dialkyl dithiophosphoric acid with base to obtain the O,O-dialkyl dithiophosphoric acid salt occurs in the substantial absence of organic solvent, thereby essentially avoiding the need to handle organic solvents or the need to filter the O,O-dialkyl dithiophosphoric acid salt composition.

A preferred embodiment of the invention comprises (a) treating an O,O-dialkyl dithiophosphoric acid of the formula

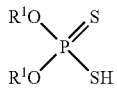

wherein each $R^1$ is independently $C_1$–$C_4$ alkyl, with a base in the presence of water and in the substantial absence of organic solvent to form (i) an organic portion and (ii) an aqueous portion containing the O,O-dialkyl dithiophosphoric acid salt, (b) separating the aqueous portion containing the O,O-dialkyl dithiophosphoric acid salt from the organic portion, and (c) treating the aqueous portion containing the O,O-dialkyl dithiophosphoric acid salt with a halothioalcohol (preferably a chlorothioalcohol).

Preferred O,O-dialkyl S-[2-(alkylthio)alkyl] phosphorodithioates obtained according to the invention include those having the formula:

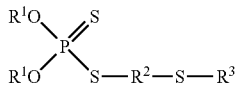

in which each $R^1$ is independently $CH_3$, $C_2H_5$, $n$-$C_3H_7$, or $i$-$C_3H_7$, $R^2$ is $CH_2$ or $C_2H_4$, and $R^3$ is $CH_3$ or $C_2H_5$.

A particularly preferred O,O-dialkyl S-[2-(alkylthio) alkyl] phosphorodithioate obtained according to the invention is O,O-diethyl S-[2-(ethylthio)-ethyl] phosphorodithioate (i.e., where each $R^1$ is $C_2H_5$, $R^2$ is $C_2H_4$, and $R^3$ is $C_2H_5$), which can be prepared by treating O,O-diethyl dithiophosphoric acid with a base in the substantial absence of organic solvent to form O,O-diethyl dithiophosphoric acid sodium salt, which is in turn treated with β-chloroethyl ethyl sulfide. This preferred product is also called phosphorodithioic acid O,O-diethyl S-[2-(ethylthio)ethyl] ester, O,O-diethyl-S-ethylmercaptoethyl dithiophosphate, and disulfoton and is available under the name Di-Syston®.

As used herein, "substantial absence of organic solvent" is intended to mean that the mixture of O,O-dialkyl dithiophosphoric acid, base and any optional ingredients, such as water, comprises no more than about 5% by weight (preferably no more than about 1% by weight) of organic solvent. Although some trace organic solvent may be present in the O,O-dialkyl dithiophosphoric acid, preferably no additional organic solvent is added to the mixture of O,O-dialkyl dithiophosphoric acid, base, and any optional ingredients.

An amount of base sufficient to provide a pH of greater than about 7 (preferably greater than about 8, more preferably about 9) is added to the O,O-dialkyl dithiophosphoric acid. In one embodiment the molar ratio of base to O,O-dialkyl dithiophosphoric acid is in the range of from about 1.05:1 to about 1.0:1 (preferably from about 1.03:1 to about 1.0:1, most preferably about 1.0:1.0). Suitable bases include alkali metal or alkaline earth metal hydroxides, ammonia, tertiary amines, and quaternary ammonium hydroxides. Preferred bases include NaOH, KOH, and ammonia. The resultant O,O-dialkyl dithiophosphoric acid salt will thus have a cation that corresponds to the base used. In preferred embodiments, the cation is an alkali metal ion, an alkaline earth metal ion (in an appropriate stoichiometric amount), ammonium ion (i.e., $NH_4^+$), or a tertiary or quaternary ammonium ion. Particularly preferred cations are $Na^+$, $K^+$, and $NH_4^+$. Typically the base is used as an aqueous composition comprising base and water, such as, for example, an aqueous solution of about 25% NaOH.

Typically the mixture of O,O-dialkyl dithiophosphoric acid and base is mixed for a time and at a temperature sufficient for the formation of the O,O-dialkyl dithiophosphoric acid salt. Suitable temperatures are in the range of from about 10° C. to about 60° C. (preferably from about 20° C. to about 35° C.), while suitable pressures are from about 700 to about 760 mm Hg (preferably from about 740 to about 760 mm Hg).

Treating the O,O-dialkyl dithiophosphoric acid with a base (preferably an aqueous base solution) in the substantial absence of (preferably in the complete absence of) organic solvent results in the formation of an organic portion, which contains any unreacted O,O-dialkyl dithiophosphoric acid and neutral organic impurities, and an aqueous portion, which contains the O,O-dialkyl dithiophosphoric acid salt. As used herein "neutral organic impurities" is intended to refer to nonionic compounds such as triesters, pyrophosphates, and disulfides. The aqueous portion can be separated from the organic portion and can be treated with the thioalcohol derivative without any extractions using organic solvents. Filtering of the aqueous portion containing the O,O-dialkyl dithiophosphoric acid salt is optional and generally not required. In a preferred embodiment the aqueous portion is not filtered prior to treatment with the thioalcohol derivative.

Suitable thioalcohol derivatives are those in which group Y is any leaving group known in the art for the reaction described herein but are preferably thioalcohol derivatives in which group Y is a halogen or a sulfonate. Suitable sulfonates include aliphatic sulfonates such as methanesulfonate and aromatic sulfonates such as benzenesulfonate or toluenesulfonate. However, preferred thioalcohol derivatives are halothioalcohols in which the halogen is chlorine. A particularly preferred halothioalcohol is β-chloroethyl ethyl sulfide.

In one embodiment the molar ratio of the thioalcohol derivative to the O,O-dialkyl dithiophosphoric acid salt is in the range of from about 1:1 to about 1.1:1 but is preferably from about 1:1 to about 1.05 and more preferably about 1:1.

Heating the aqueous portion containing the O,O-dialkyl dithiophosphoric acid salt with the thioalcohol derivative occurs at a pH of less than about 7 (preferably about 6). The pH can be adjusted with an suitable pH adjuster, including alkali metal hydroxides, such as NaOH and KOH.

Typically the aqueous portion is heated for a time and at a temperature sufficient for the formation of the O,O-dialkyl S-[2-(alkylthio)alkyl] phosphorodithioate. Suitable temperatures are in the range of from about 30° C. to about 85° C. (preferably from about 65° C. to about 75° C.), while suitable pressures are from about 700 to about 760 mm Hg (preferably from about 740 to about 760 mm Hg).

The reaction of the O,O-dialkyl dithiophosphoric acid salt with the thioalcohol derivative does not require the presence of a metal catalyst, such as zinc chloride, ferrous chloride, or stannous chloride, and preferably occurs in the substantial absence of a metal catalyst. As used herein, "substantial absence of metal catalyst" is intended to mean that the mixture of the aqueous portion containing the O,O-dialkyl dithiophosphoric acid salt and the halothioalcohol comprises no more than 0.1% (preferably no more than 0.01%) by weight, metal catalyst. It is particularly preferred to carry out the reaction in the complete absence of metal catalyst.

Treatment of the aqueous portion containing the O,O-dialkyl dithiophosphoric acid salt with the thioalcohol derivative and heat results in the formation of an aqueous phase and an organic phase containing the O,O-dialkyl S-[2-(alkylthio)alkyl] phosphorodithioate. The O,O-dialkyl S-[2-(alkylthio)alkyl] phosphorodithioate can be isolated from the organic phase using any suitable method. For example, the organic phase can be washed with water and then dried to obtain the O,O-dialkyl S-[2-(alkylthio)alkyl] phosphorodithioate. The dry O,O-dialkyl S-[2-(alkylthio)alkyl] phosphorodithioate can be subjected to a purge using air or an inert gas, such as nitrogen, to decrease the level of any remaining volatile by-products or contaminants, such as sulfur dioxide, chloroethane, ethanethiol, ethyl vinyl sulfide, or ethyl sulfide.

In one embodiment of the invention, an O,O-dialkyl dithiophosphoric acid is treated with base in the presence of water and in the substantial absence of organic solvent to form an organic portion and an aqueous portion containing O,O-dialkyl dithiophosphoric acid salt. The aqueous portion is separated from the organic portion and then heated with a chlorothioalcohol, thereby forming an aqueous phase and an organic phase containing the O,O-dialkyl S-[2-(alkylthio)alkyl] phosphorodithioate. The organic phase can be washed with water and dried to obtain the O,O-dialkyl S-[2-(alkylthio)alkyl] phosphorodithioate. The dry O,O-dialkyl S-[2-(alkylthio)alkyl] phosphorodithioate can be subjected to a purge using air or an inert gas, such as nitrogen, to decrease the level of any remaining volatile by-products or contaminants, such as sulfur dioxide, chloroethane, ethanethiol, ethyl vinyl sulfide, or ethyl sulfide.

In another embodiment of the invention, O,O-diethyl dithiophosphoric acid is treated with a base in the substantial absence of (preferably the absence of) organic solvent to form O,O-diethyl dithiophosphoric acid salt, followed by reaction of the O,O-diethyl dithiophosphoric acid salt with β-chloroethyl ethyl sulfide to obtain O,O-diethyl S-[2-(ethylthio)ethyl] phosphorodithioate. If the base is an aqueous solution of sodium hydroxide, then O,O-diethyl dithiophosphoric acid sodium salt is formed.

In a preferred embodiment of the invention the O,O-diethyl dithiophosphoric acid is treated with a base in the presence of water and in the substantial absence of organic solvent, thereby forming an organic portion and an aqueous portion containing O,O-diethyl dithiophosphoric acid salt. The aqueous portion containing O,O-diethyl dithiophosphoric acid salt is separated from the organic portion. The aqueous portion in then mixed with β-chloroethyl ethyl sulfide and heated, thereby forming an aqueous phase and an organic phase containing the O,O-diethyl S-[2-(ethylthio)ethyl] phosphorodithioate. The organic phase can be washed with water and dried to recover the O,O-diethyl S-[2-(ethylthio)ethyl] phosphorodithioate. The dry O,O-diethyl S-[2-(ethylthio)ethyl] phosphorodithioate can be subjected to a purge using air or an inert gas, such as nitrogen, to decrease the level of any remaining volatile by-products or contaminants.

The methods of the present invention can be used to prepare O,O-dialkyl dithiophosphoric acid salts. An O,O-dialkyl dithiophosphoric acid is treated with a base in the presence of water and in the substantial absence of organic solvent, thereby forming an organic portion and an aqueous portion containing O,O-dialkyl dithiophosphoric acid salt. The aqueous portion containing O,O-dialkyl dithiophosphoric acid salt is separated from the organic portion and the O,O-dialkyl dithiophosphoric acid salt is isolated from the aqueous composition. Any suitable isolation method can be used, such as, for example, evaporation of the water.

Throughout the examples and the present specification, parts and percentages are by weight unless otherwise specified. The following examples are illustrative only and are not intended to limit the scope of the methods of the invention as defined by the claims.

EXAMPLES

Example 1

Inventive Method

About 372 g of O,O-diethyl dithiophosphoric acid was placed in a 1 liter four-neck round bottom flask equipped with a mechanical agitator, dropping funnel, pH probe, thermometer, and condenser. About 320 g of an aqueous solution of 25% by weight of NaOH was added over about 5 hours until the pH was about 9. The temperature of the reaction mixture was kept in the range of from about 26° C. to about 32° C. using an ice bath as necessary. The reaction was agitated until about 15 minutes after the base addition was finished. About 140 g of water was added and the mixture was stirred for about 5 minutes. A composition containing O,O-diethyl dithiophosphoric acid sodium salt was obtained.

The composition containing O,O-diethyl dithiophosphoric acid sodium salt was allowed to separate into an aqueous portion and an organic portion. The aqueous portion was collected. About 250 ml of the aqueous portion was placed in a 500 ml four-neck round bottom flask and heated to about 70° C. under nitrogen. About 89.6 g of β-chloroethyl ethyl sulfide (93% purity) was added over about 30 minutes. The resulting mixture was stirred for about 3.5 hours. The pH was maintained at about 6 with 50% by weight NaOH. The mixture was filtered hot under vacuum. The upper organic phase was collected and washed with about 173 g of water. The product was dried by rotary evaporation at about 65° C. under aspirator vacuum for about 3 hours. About 0.67 g of O,O-diethyl S-[2-(ethylthio)ethyl] phosphorodithioate (96.9% purity) was obtained.

Example 2

Comparative Method

A composition containing O,O-diethyl dithiophosphoric acid sodium salt was obtained by mixing O,O-diethyl dithiophosphoric acid with an about 25% by weight of NaOH solution in the presence of toluene.

About 250 g of the composition containing O,O-diethyl dithiophosphoric acid sodium salt was placed in a separatory funnel, and about 5.1 g of toluene was added with agitation. The mixture was filtered before separation and the lower aqueous phase was collected.

About 250 ml of the aqueous phase was placed in a 500 ml four-neck round bottom flask and heated to about 70° C. under nitrogen. About 89.6 g of β-chloroethyl ethyl sulfide (93% purity) was added over about 30 minutes. The resulting mixture was stirred for about 3.5 hours. The pH was maintained at about 6 with 50% by weight NaOH. The mixture was filtered hot under vacuum. The upper organic phase was collected and washed with about 173 g of water.

The final product was dried by rotary evaporation at about 65° C. under aspirator vacuum for about 3 hours. About 0.71 g of O,O-diethyl S-[2-(ethylthio)ethyl] phosphorodithioate (97.2% purity) was obtained.

Thus the method in accordance with the invention, when compared with a know method, provided good yield and purity of O,O-diethyl S-[2-(ethylthio)ethyl] phosphorodithioate without requiring the step of filtering and separation of the composition containing the O,O-diethyl dithiophosphoric acid sodium salt.

Additional embodiments and modifications within the scope of the claimed invention will be apparent to one of ordinary skill in the art. Accordingly, the scope of the present invention shall be considered in terms of the following claims, and is understood not to be limited to the details of the methods described in the specification.

What is claimed is:

1. A method of preparing an O,O-dialkyl S-[2-(alkylthio) alkyl] phosphorodithioate having the formula

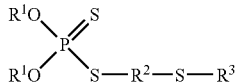

wherein
each $R^1$ is independently $C_1$–$C_4$ alkyl,
$R^2$ is $C_1$–$C_4$ alkylene, and
$R^3$ is $C_1$–$C_4$ alkyl,
comprising
(a) treating an O,O-dialkyl dithiophosphoric acid of the formula:

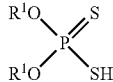

wherein each $R^1$ is independently $C_1$–$C_4$ alkyl, with a base in the substantial absence of organic solvent to obtain an O,O-dialkyl dithiophosphoric acid salt of the formula:

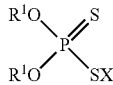

wherein
each $R^1$ is independently $C_1$–$C_4$ alkyl, and
X is a cation, and
(b) reacting the O,O-dialkyl dithiophosphoric acid salt with a thioalcohol derivative having the formula:

wherein
$R^2$ is $C_1$–$C_4$ alkylene,
$R^3$ is $C_1$–$C_4$ alkyl, and
Y is a leaving group.

2. A method according to claim 1 wherein each $R^1$ is independently $CH_3$, $C_2H_5$, n-$C_3H_7$, or i-$C_3H_7$; $R^2$ is $CH_2$ or $C_2H_4$; and $R^3$ is $CH_3$ or $C_2H_5$.

3. A method according to claim 1 wherein $R^1$ is $C_2H_5$, $R^2$ is $C_2H_4$, and $R^3$ is $C_2H_5$.

4. A method according to claim 1 wherein the base is an alkali metal hydroxide.

5. A method according to claim 1 wherein the base is NaOH.

6. A method according to claim 1 wherein Y is a halogen or a sulfonate.

7. A method according to claim 1 wherein Y is chlorine.

8. A method according to claim 1 further comprising separating the O,O-dialkyl dithiophosphoric acid salt from any unreacted O,O-dialkyl dithiophosphoric acid and neutral organic impurities.

9. A method according to claim 1 comprising
(a) treating the O,O-dialkyl dithiophosphoric acid with a base in the presence of water and in the substantial absence of organic solvent to form (i) an organic portion and (ii) an aqueous portion containing the O,O-dialkyl dithiophosphoric acid salt,
(b) separating the aqueous portion containing the O,O-dialkyl dithiophosphoric acid salt from the organic portion, and
(c) treating the aqueous portion containing the O,O-dialkyl dithiophosphoric acid salt with a halothioalcohol.

10. A method according to claim 1 wherein the O,O-dialkyl dithiophosphoric acid is treated with an amount of base sufficient to provide a pH greater than about 7.

11. A method according to claim 1 wherein the O,O-dialkyl dithiophosphoric acid is treated with an amount of base sufficient to provide a pH of about 9.

12. A method according to claim 1 of preparing O,O-diethyl S-[2-(ethylthio)ethyl] phosphorodithioate comprising
(a) treating O,O-diethyl dithiophosphoric acid with a base in the substantial absence of organic solvent to form an O,O-diethyl dithiophosphoric acid salt, and
(b) reacting the O,O-diethyl dithiophosphoric acid salt with β-chloroethyl ethyl sulfide.

13. A method according to claim 12 comprising
(a) treating the O,O-diethyl dithiophosphoric acid with a base in the presence of water and in the substantial absence of organic solvent to form an organic portion and an aqueous portion containing O,O-diethyl dithiophosphoric acid salt,
(b) separating the aqueous portion comprising O,O-diethyl dithiophosphoric acid salt from the organic portion, and
(c) treating the aqueous portion containing O,O-diethyl dithiophosphoric acid salt with β-chloroethyl ethyl sulfide.

14. A method according to claim 12 wherein the base is sodium hydroxide.

15. A method according to claim 12 wherein the O,O-diethyl dithiophosphoric acid salt is reacted with β-chloroethyl ethyl sulfide in the substantial absence of a metal catalyst.

16. A method according to claim 1 of preparing an O,O-dalkyl S-[2-(alkylthio)alkyl] phosphorodithioate having the formula

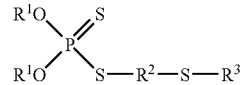

wherein
each $R^1$ is independently $CH_3$, $C_2H_5$, n-$C_3H_7$, or i-$C_3H_7$,
$R^2$ is $CH_2$ or $C_2H_4$, and
$R^3$ is $CH_3$ or $C_2H_5$,
comprising
(a) treating an O,O-dialkyl dithiophosphoric acid of the formula:

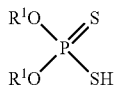

wherein each $R^1$ is independently $CH_3$, $C_2H_5$, n-$C_3H_7$, or i-$C_3H_7$, with a base in the presence of water and in the substantial absence of organic solvent to form an organic portion and an aqueous portion containing O,O-dialkyl dithiophosphoric acid salt of the formula:

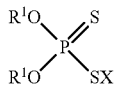

wherein
each $R^1$ is independently $CH_3$, $C_2H_5$, n-$C_3H_7$, or i-$C_3H_7$, and
X is a cation, and (b) separating the aqueous portion containing the O,O-dialkyl dithiophosphoric acid salt, and
(c) heating the aqueous portion containing the O,O-dialkyl dithiophosphoric acid salt with a halothioalcohol having the formula

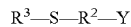

wherein
$R^2$ is $CH_2$ or $C_2H_4$,
$R^3$ is $CH_3$ or $C_2H_5$, and
Y is a halogen.

17. A method according to claim 16 wherein $R^1$ is $C_2H_5$, $R^2$ is $C_2H_4$, and $R^3$ is $C_2H_5$.

18. A method according to claim 16 wherein the O,O-dialkyl dithiophosphoric acid is treated with an amount of base sufficient to provide a pH of greater than about 7.

19. A method according to claim 16 wherein the aqueous portion containing the O,O-dialkyl dithiophosphoric acid salt is heated with a halothioalcohol at a pH of less than about 7.

20. A method according to claim 16 additionally comprising
(d) washing the organic phase with water, and
(e) drying the organic phase to obtain the O,O-dialkyl S-[2-(alkylthio)alkyl] phosphorodithioate.

21. A method according to claim 20 further comprising
(f) subjecting the O,O-dialkyl S-[2-(alkylthio)alkyl] phosphorodithioate to a purge using air or an inert gas.

* * * * *